US011585750B2

(12) United States Patent
Bock et al.

(10) Patent No.: US 11,585,750 B2
(45) Date of Patent: Feb. 21, 2023

(54) ARRANGEMENT FOR DETERMINING BODY SURFACE PROPERTIES BY MEANS OF MULTIPLE SPATIALLY RESOLVED REFLECTION SPECTROSCOPY (MSRRS)

(71) Applicant: Henkel AG & Co. KGaA, Duesseldorf (DE)

(72) Inventors: Andreas Bock, Neuss (DE); Thomas Welss, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 330 days.

(21) Appl. No.: 16/652,360

(22) PCT Filed: Sep. 25, 2018

(86) PCT No.: PCT/EP2018/075944
§ 371 (c)(1),
(2) Date: Mar. 30, 2020

(87) PCT Pub. No.: WO2019/086173
PCT Pub. Date: May 9, 2019

(65) Prior Publication Data
US 2020/0300754 A1 Sep. 24, 2020

(30) Foreign Application Priority Data
Nov. 6, 2017 (DE) ...................... 10 2017 219 625.4

(51) Int. Cl.
*G01N 21/33* (2006.01)
*G16H 70/20* (2018.01)
(Continued)

(52) U.S. Cl.
CPC .......... *G01N 21/33* (2013.01); *A61B 5/0075* (2013.01); *A61B 5/44* (2013.01); *A61B 5/443* (2013.01);
(Continued)

(58) Field of Classification Search
CPC .... G01N 21/35; G01N 21/3103; A61B 5/443; A61B 5/0075; G16H 70/20
See application file for complete search history.

(56) References Cited

U.S. PATENT DOCUMENTS 9,239,289 B1    1/2016  Goldan
10,416,079 B2 *  9/2019  Magnussen .......... A61B 5/1455
(Continued)

FOREIGN PATENT DOCUMENTS

CN       105488577 A  *  4/2016
DE     102012005583 A1     5/2013
(Continued)

OTHER PUBLICATIONS

EPO, International Search Report issued in International Application No. PCT/EP2018/075944, dated Jan. 7, 2019.
(Continued)

*Primary Examiner* — Maurice C Smith
(74) *Attorney, Agent, or Firm* — Lorenz & Kopf, LLP

(57) ABSTRACT

An arrangement and a computer program product are provided for determining body surface characteristics. An arrangement includes an acquisition unit configured to detect body surface features by Multiple Spatially Resolved Reflection Spectroscopy (MSRRS) in a wavelength range between about 300 nm and about 1500 nm; a data storage unit to interrogate data using the characteristics; and a user interface comprising an output unit, wherein the user interface is configured to interact with a user. Further, the arrangement includes a portable computing unit configured for: interacting with a user and for evaluating the features and for determining the characteristics based on the features; obtaining from the data storage unit features of treatment products and/or application instructions for non-therapeutic treatment of a body surface according to the characteristics;
(Continued)

and instructing the output unit to output information on the treatment products and/or application instructions to a user.

13 Claims, 3 Drawing Sheets

(51) Int. Cl.
| | | |
|---|---|---|
| *A61B 5/00* | (2006.01) | |
| *G01N 21/35* | (2014.01) | |
| *G06Q 10/0631* | (2023.01) | |
| *G06Q 30/0601* | (2023.01) | |
| *A45D 44/00* | (2006.01) | |

(52) U.S. Cl.
CPC .............. *A61B 5/448* (2013.01); *G01N 21/35* (2013.01); *G06Q 10/06316* (2013.01); *G06Q 30/0623* (2013.01); *G06Q 30/0631* (2013.01); *G06Q 30/0633* (2013.01); *G16H 70/20* (2018.01); *A45D 2044/007* (2013.01); *G01N 2201/062* (2013.01); *G01N 2201/06113* (2013.01)

(56) References Cited

U.S. PATENT DOCUMENTS

| | | | |
|---|---|---|---|
| 2007/0167853 A1* | 7/2007 | Melker | A61B 5/411 |
| | | | 600/529 |
| 2017/0119130 A1 | 5/2017 | Witchell et al. | |

FOREIGN PATENT DOCUMENTS

| | | | | |
|---|---|---|---|---|
| DE | 102017203499 A1 * | 7/2017 | ............. | A61B 5/082 |
| FR | 2836367 A1 * | 8/2003 | ........... | A61B 5/0071 |
| WO | WO-2009142758 A1 * | 11/2009 | ........... | A61B 5/0062 |

OTHER PUBLICATIONS

Darvin et al.: "Multiple spatially resolved reflection spectroscopy for in vivo determination of carotenoids in human skin and blood", Laser Physics Letters, Germany, vol. 13, No. 9, Aug. 2016, p. 2-4, XP055534301.

* cited by examiner

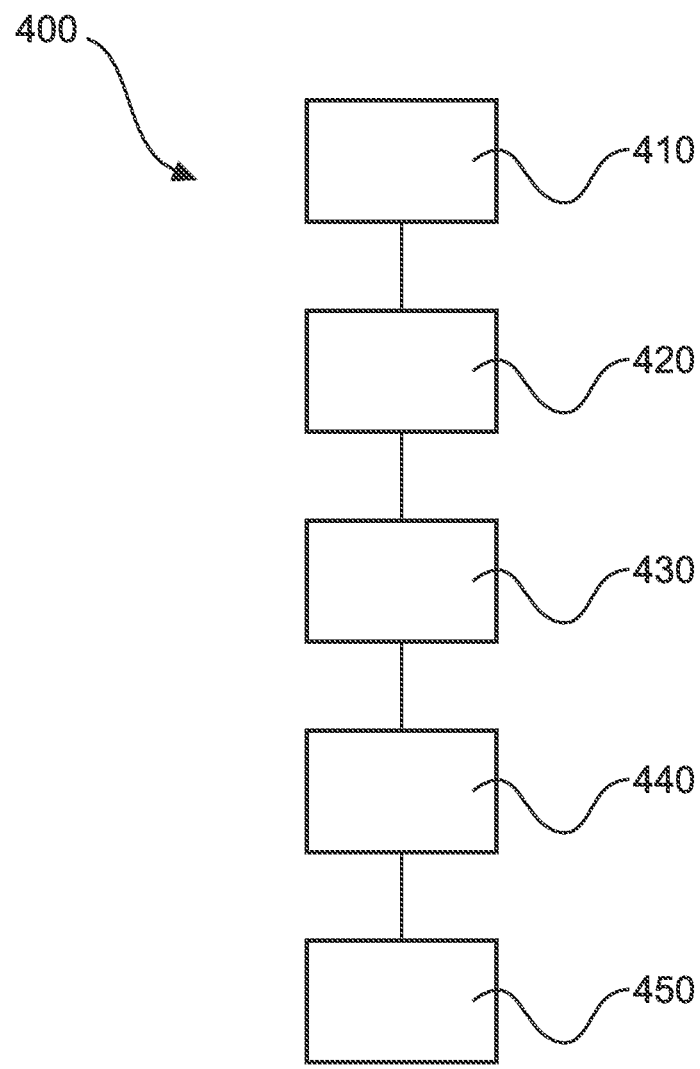

ARRANGEMENT FOR DETERMINING BODY SURFACE PROPERTIES BY MEANS OF MULTIPLE SPATIALLY RESOLVED REFLECTION SPECTROSCOPY (MSRRS)

CROSS-REFERENCE TO RELATED APPLICATION

This application is a U.S. National-Stage entry under 35 U.S.C. § 371 based on International Application No. PCT/EP2018/075944, filed Sep. 25, 2018, which was published under PCT Article 21(2) and which claims priority to German Application No. 10 2017 219 625.4, filed Nov. 6, 2017, which are all hereby incorporated in their entirety by reference.

TECHNICAL FIELD

The present disclosure concerns a set-up or arrangement for determining body surface characteristics and a computer program product which is configured to be executed on a portable computing unit.

BACKGROUND

In many areas of daily life, there has been a recent trend towards personalized programs that specifically address individual prerequisites and needs (e.g. in the areas of nutrition or health). But this also applies to personalized cosmetics. The aim here is to enable consumers to find specific products or receive treatment instructions tailored to their individual needs. Accordingly, it is desirable to provide user-friendly and effective approaches for determining non-therapeutic treatment of the body surface as well as a set-up implementing such approaches.

BRIEF SUMMARY

It can be considered as a task of the present disclosure to describe a set-up or arrangement which enables a user, in particular a consumer or end user, to obtain individually tailored recommendations for non-therapeutic treatment products and instructions for non-therapeutic treatment of the body surface.

This task is solved with the features of independent Claims. Further developments of the present disclosure result from the dependent Claims and from the following description.

According to an exemplary embodiment a set-up or arrangement for determining body surface characteristics is provided. The arrangement comprises an acquisition unit an acquisition unit configured to detect body surface features by Multiple Spatially Resolved Reflection Spectroscopy (MSRRS) in a wavelength range between about 300 nm and about 1500 nm; a data storage unit to interrogate data using the determined body surface characteristics; and a user interface comprising an output unit, wherein the user interface is configured to interact with a user. Further, the exemplary arrangement includes a portable computing unit configured for: interacting with a user and for evaluating the determined body surface features and for determining the body surface characteristics based on the determined body surface features; obtaining from the data storage unit features of treatment products and/or application instructions for non-therapeutic treatment of a body surface according to the determined body surface characteristics; and instructing the output unit to output information on the treatment products and/or application instructions to a user.

According to another exemplary embodiment, a computer program product is configured to be executed on a portable computing device and is configured to instruct a processor of the portable computing device to perform the following steps: detecting body surface features of a user by employing Multiple Spatially Resolved Reflection Spectroscopy in a wavelength range between about 300 nm and about 1500 nm; evaluating the detected body surface features and determining body surface characteristics based on the detected body surface features; interrogating a data storage unit using the determined body surface characteristics; obtaining features of treatment products and/or application instructions for non-therapeutic treatment of a body surface according to the determined body surface characteristics from the data storage unit; and instructing the output unit to output information on the treatment products and/or application instructions.

BRIEF DESCRIPTION OF THE DRAWINGS

The present disclosure will hereinafter be described in conjunction with the following drawing figures, wherein like numerals denote like elements, and:

FIG. 2 a schematic illustration of a computer program product according to a further exemplary embodiment;

FIG. 3 a schematic illustration of a method executed by a computer program product according to an exemplary embodiment;

DETAILED DESCRIPTION

Figure 1:
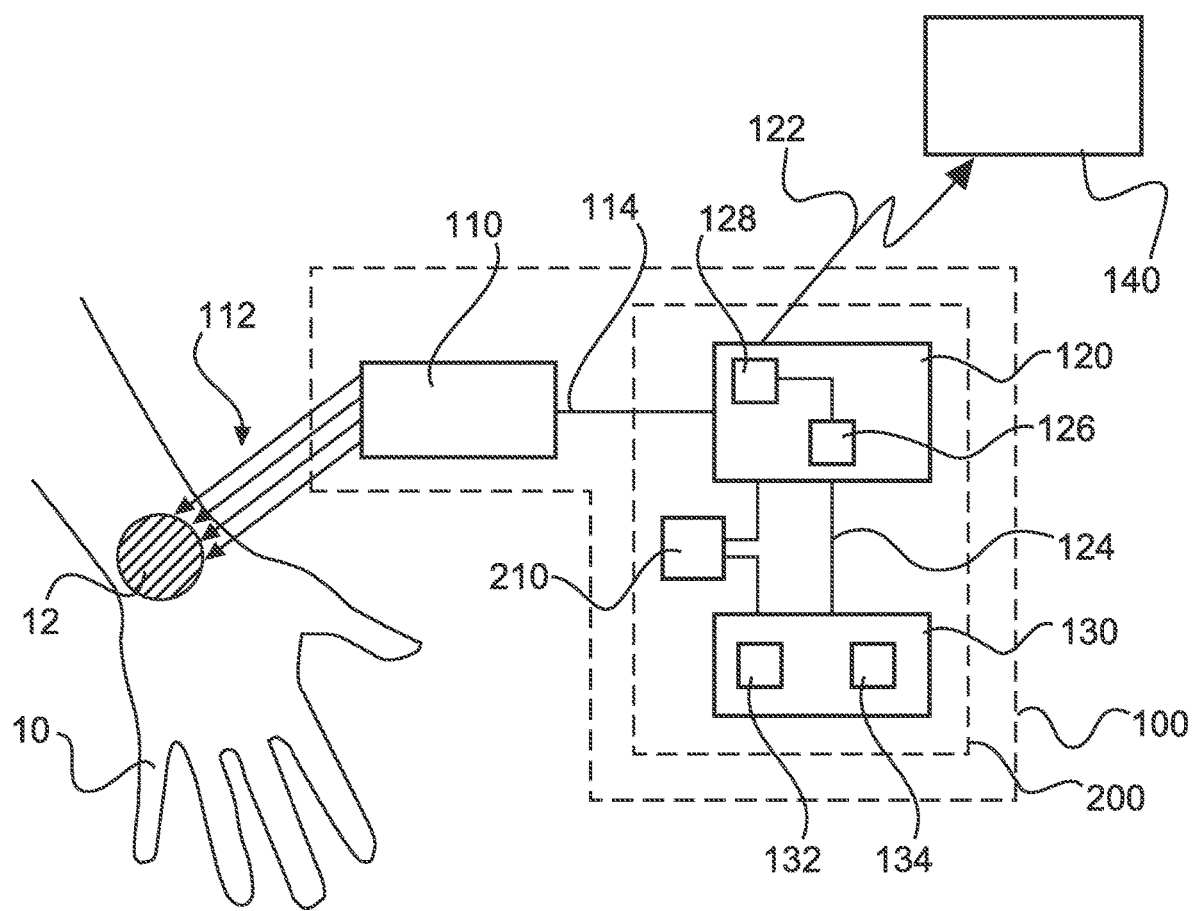
FIG. 1 a schematic illustration of a set-up or arrangement for determining body surface characteristics according to an exemplary embodiment.

The following detailed description is merely exemplary in nature and is not intended to limit the disclosure or the application and uses of the subject matter as described herein. Furthermore, there is no intention to be bound by any theory presented in the preceding background or the following detailed description.

For a consumer of cosmetic products it is difficult or impossible to assess in a standardized and objective manner the success of a non-therapeutic treatment with cosmetic products at home. On the one hand, this makes it more difficult for the consumer to check the individual effectiveness of a cosmetic product and, on the other hand, it reduces the motivation to carry out a corresponding treatment in the long term.

In many areas of daily life, there has been a trend towards personalized programs that specifically address individual requirements and needs (e.g. in the areas of nutrition or health). But this also applies to personalized cosmetics. The aim is to enable consumers to find specific products or receive treatment instructions tailored to the individual needs of their skin.

Multiple Spatially Resolved Reflection Spectroscopy (MSRRS) uses the principle of Spatially Resolved Spectroscopy (SRS) by combining many light emitters of different wavelengths with many light detectors on one skin area. In Spatially Resolved Spectroscopy, the light intensity is measured as a function of the distance to a light source. Here, for example, light in a wavelength range between about 300 nm and about 1500 nm, especially between about 350 nm and about 1000 nm, further especially between about 440 nm and about 490 nm is used. Light can penetrate deep into the skin and is scattered and absorbed by components of the skin. Absorption and scattering depend on the wavelength and on the substances in the skin and their specific spectral absorption ranges. Through the multiple use of Spatially Resolved Spectroscopy (SRS), light that has penetrated deep into the skin can be compared with light that has only passed through the outer layers of the skin. In MSRRS, the principle of SRS is applied several times, for example by combining many light emitters of different wavelengths with many light detectors of different wavelengths on one area of skin. This increases the measurement accuracy and is helpful for an exact measurement due to the complexity and inhomogeneity of the skin. The accuracy can be further improved by varying the angle of incidence of the light emitters. From the light measured by Multiple Spatially Resolved Reflection Spectroscopy (MSRRS), the concentration of antioxidants, e.g. non-enzymatic antioxidants and/or carotenoids, in the skin can be determined. Influences of other chromophores in the skin, e.g. melanin or hemoglobin, can be eliminated by using wavelengths that are not absorbed by carotenoids. MSRRS measures in particular diffuse reflected light.

By employing a measuring device (namely the acquisition unit) based on Multiple Spatially Resolved Reflection Spectroscopy (MSRRS), which is connected as a device to or integrated into a portable personal device of a user such as a smartphone, tablet or other computer unit (these units can be generally referred to as a computing unit or portable computing unit), cosmetically relevant parameters of the skin are measured, in particular the content of antioxidants. Cosmetically relevant parameters of hair can also be measured. In a computer program product (e.g. software or application for the personal/portable device), the parameters are then displayed in the form of values, arbitrary units or a verbal derivation. From the parameters, (a) product recommendations for individually suitable treatment products and individual treatment recommendations can then be derived and/or (b) the treatment success in a cosmetic or pharmaceutical treatment, which has the objective of positively influencing the measured parameters, in particular the content of antioxidants in the skin, can be determined and/or displayed.

The measuring device may have an interface via which a connection to the computing unit is established. The computing unit may include a first interface and a second interface. The first interface may be configured as a counterpart to the interface of the measuring device, i.e. to connect the measuring device to the computing unit. The second interface may be configured to connect the computing unit to a data network (see FIG. 1). These connections are configured to transmit information in at least one direction, preferably in both directions. The connection between the measuring device and the computing unit on the one hand and the connection between the computing unit and an access point of the data network may be wired or wireless. Wired connections may, for example, use optical or electrical signals for information transmission. Wireless connections typically use electromagnetic waves for signal transmission, for example radio signals or optical signals.

Protocols that work according to the principles of mesh networks can be used to connect the measuring device to the computing unit. For example, the Thread protocol based on IPv6 may be used for data transmission and for connecting the measuring device to the computing unit. The Thread protocol is used in particular to connect automated or semi-automated devices.

In an example, the measuring device may be structurally plugged onto the computing unit. This means that the measuring device is mechanically attached to the computing unit or an enclosure of the computing unit. This may be done, for example, by mounting it without tools via a reversible connection. In the attached position, the measuring device may be held relative to the computing unit with a detachable frictional or positive connection. The interfaces between the measuring device and the computing unit may be configured in such a way that an electrical connection between the measuring device and the computing unit is automatically established or established in the mounted position.

The computing unit may execute an application (or program) that receives or interrogates data from the measuring device. The received or interrogated data is used in the application to determine one or more output values. The data is processed and/or evaluated by the application according to the approaches described herein.

To run the application, processors (and one or more memory modules) of the computing unit may be used. The computing unit may also be configured to outsource calculation steps for executing the application. For example, the application may transfer the data received or interrogated from the measuring device to an external computing unit. Before the data is transferred to the external computing unit, it may undergo pre-processing.

The external computing unit may be located at a distance from the measuring device and the portable computing unit. The portable computing unit may be connected to the external computing unit via the data network, that is, it may have a communication link. The external computing unit may be a single computer or processor or a combination of computers or processors. In a computer or processor group, the computing load may be distributed to the individual components of the group from various perspectives. In addition to computing power, this computer network may also provide storage capacity for the users and may hold data released or marked by the users. In this way, the storage space required in the portable computing unit may be reduced. It is also made easier for the user to exchange a portable computing unit because no or almost no data is stored locally. The computer network may be configured as a group of meshed networked servers.

The computer program product enables the control and tracking of the results by displaying (e.g. graphically) the measurement results over time. The computer program product provides individual treatment and product recommendations based on the results obtained. The quality of the treatment and product recommendations may be improved by the user additionally answering questions about his skin or hair condition, nutritional habits, general health condition and other behaviors that the computer program product processes accordingly. For this purpose not only e.g. literature data are taken as a basis, but also the treatment success of other users of the computer program product, in particular treatment successes of other users who have at least a similar skin condition.

The data captured by employing the questionnaire may be used to analyze a development of the condition of the user's skin and hair under the given circumstances, i.e. the data entered by the user. This development may be compared with the development of other users. From this, it can be concluded whether, during a treatment with a certain treatment product, the development of users with similar or identical entries in the questionnaire is the same or differs from users with other entries.

In this way, for example, the influence of a certain fact on the success of the treatment may be concluded. If the development of a skin parameter in several smokers with certain cigarette consumption (e.g. about 10 cigarettes per day) shows a significant deviation from the development of the same skin parameter in non-smokers, it can be concluded that smoking has an effect on the certain parameter in a way that can be quantified. Alternatively, it can be concluded that a different product or treatment is recommended for smokers.

The data entered by the user may thus be used for a global analysis in order to monitor the success of a treatment and the effectiveness of a product under different conditions and, if necessary, to recommend changes in the treatment and/or product.

It is possible to present the questionnaire to the user at periodically recurring times and to ask for changes. Under certain circumstances, it is also conceivable to give advice on the interrogated information. For example, a recommendation could be to extend the length of sleep, to reduce the use of stimulants (alcohol, cigarettes) or to adjust other lifestyle habits.

The present disclosure enables the control and follow-up of the efficacy of a cosmetic and pharmaceutical treatment in an objective and standardized manner, which has the particular aim of increasing the content of antioxidants in the skin, e.g. in the area of prevention, reduction or elimination of skin ageing or of signs of skin ageing. The effectiveness of the (cosmetic, non-therapeutic) treatment may be better understood and thus the selection of an individually suitable product may be simplified.

The present disclosure makes it possible to obtain individual treatment and product recommendations that meet the needs of the individual user and increases the motivation to carry out a cosmetic treatment over a longer period of time, also by comparing it with other users and/or by observing the development of one's own skin or hair.

It is an aspect of the set-up that the equipment required for this is handheld, i.e. operable and portable in one hand. For example, the display unit has a surface area of up to 36 cm$^2$, but may also be larger. In particular, the acquisition unit is configured to capture body surface features using Multiple Spatially Resolved Reflection Spectroscopy (MSRRS) in a wavelength range between about 300 nm and about 1500 nm, preferably from about 350 nm to about 1000 nm, especially between about 440 nm and about 490 nm.

All skin and hair parameters measurable by Multiple Spatially Resolved Reflection Spectroscopy (MSRRS), preferably human skin and hair, may be used as measurement parameters, especially the presence of antioxidants such as carotenoids.

Antioxidants are a heterogeneous group of chemical substances which can inactivate free radicals, especially reactive oxygen species, as radical scavengers. Free radicals are continuously formed throughout the human body and can lead to oxidative stress if they are too concentrated. Tobacco consumption, UV radiation, air pollution, stress and other external influences can induce the formation of free radicals and lead to oxidative stress. Free radicals can, for example, cause damage to DNA or membranes and inactivate enzymes. Free radicals play an important role in skin aging, especially in extrinsic aging.

The skin contains a number of enzymatic and non-enzymatic antioxidants. An important group of non-enzymatic antioxidants are the carotenoids which are particularly found in the horny layer (stratum corneum) and whose content in the skin correlates with nutritional and lifestyle habits. The antioxidant content physiologically decreases with age.

Antioxidants are used in a number of anti-ageing products, e.g. in facial care, but also in sun protection products, as UV radiation generates a particularly high number of free radicals.

Based on the measurement results, the user can be given treatment and/or specific product recommendations, especially if the specific parameter, e.g. the carotenoid content, is outside the target value or normal range.

If the user has a low antioxidant level, especially carotenoid content, he may receive the treatment recommendation to avoid sun and/or solarium. In addition or alternatively, products with high antioxidant content may be recommended. In addition or as an alternative to carotenoids, these products may include tocopherols, ascorbic acid, polyphenols (e.g. propyl gallate, elagic acid, flavonoids or epigallocatechin], carrot extracts and/or dimethylmethoxy chromanol A further recommendation may include products with a high SPF (for example >25 SPF). Products with a high SPF may include as ingredients, for example, benzophenone-3, benzophenone-4, benzophenone-5, 3-benzylidene camphor, benzylidene camphor sulfonic acid, bis-ethylhexyloxyphenol-methoxyphenyltriazine (BEMT), butylmethoxydibenzoylmethane (BMDM, avobenzone), diethylhexylbutamidotriazone, dimethicodiethylbenzalmalonate, dimethyl pabamidopropyllaurdimonium tosylate, drometrizoltrisiloxane (DTS), ethylhexyldimethyl PABA, ethylhexylmethoxycinnamate, ethylhexyl salicylate (EHS), homosalates, isoamyl p-ethoxycinnamate, isopropylbenzylsalicylate, 4-methylbenzylidene camphor, methylene-bis-benzotriazolyl-tetramethylbutylphenol (MBBT), octocrylene (OC), octyltriazone, PABA, PEG-25 PABA, phenylbenzimidazole sulfonic acid (PBSA), disodium phenyldibenzimidazole tetrasulfonate (DPDT), polyacrylamidomethylbenzylidene camphor, terephthalide-dicamphor sulfonic acid (TDSA) and salts and/or titanium dioxide.

FIG. 1 shows a set-up or arrangement 100 for determining skin characteristics. The set-up or arrangement 100 includes an acquisition unit 110, an evaluation unit 120 and a user interface 130. The acquisition unit 110 is configured to acquire characteristics of a body surface of a human user by employing Multiple Spatially Resolved Reflection Spectroscopy (MSRRS). For this purpose, the acquisition unit 110 emits at least two different electromagnetic waves 112 from at least two light emitters (see FIG. 4) in the direction of a surface area 12 of the analysis object 10 to be examined (for example, the human hand or generally a section of the body surface). The light emitters may be lasers or light-emitting diodes (LEDs); a light emitter may be referred to as a light source. In particular, a matrix including individual light sources may be provided. The electromagnetic waves reflected by the surface area 12 to be examined (not shown) are picked up by the acquisition unit 110 and allow conclusions to be drawn about the composition and structure of the surface area 12 to be examined Hair may also be examined instead of human skin. The acquisition unit 110 includes at least two suitable sources of electromagnetic waves. These sources may also be called radiation sources or light emitters and are located on or in the acquisition unit 110. The radiation source may be located at or in the acquisition unit 110 in such a way that, when the electromagnetic waves 112 are emitted, the radiation sources are at a predetermined distance from the surface area 12 to be examined, especially when the acquisition unit 110 is placed on the surface area 12 to be examined. The distance of the radiation sources from the surface region to be examined may vary and may be changed by employing actuators or manually.

The acquisition unit 110 is connected to the evaluation unit 120 via a data transmission connection 114. The data transmission connection 114 can enable unidirectional or bidirectional data transmission between the acquisition unit 110 and the evaluation unit 120. Thus the acquisition unit 110 delivers signals concerning the detected features of skin or hair to the evaluation unit 120, whereas the evaluation unit 120 can deliver control commands to the acquisition unit 110, whereby the control commands specify how the acquisition unit 110 operates. In the case of a unidirectional data transmission connection 114, which only allows data transmission from the acquisition unit 110 to the evaluation unit 120, control parameters may be specified via input elements (buttons, switches, rotary knobs, etc., not shown) on the acquisition unit 110. The acquisition unit 110 may have display elements (not shown), which indicate a status of the acquisition unit or the set control parameters. Alternatively, the acquisition unit 110 may also transmit the set control parameters to the evaluation unit 120, where they may be optionally displayed.

The evaluation unit 120 includes a processor 126 and a local memory 128. The evaluation unit 120 receives signals concerning the features of the examined surface area 12 and determines a recommendation for a non-therapeutic treatment of the examined surface area based on these features. The non-therapeutic treatment may include recommendations for treatment products and/or care instructions or application instructions for the respective surface area under examination. Care and application instructions are used as synonyms in the context of this description and refer to instructions for the non-therapeutic treatment of the examined surface area 12 using selected treatment products or even without the use of treatment products. In particular, treatment instructions may include the use of a treatment product, or measures to be taken or not to be taken by the user. For example, the treatment instructions may contain an indication of desired or undesired behavior after the application of a treatment product. In order to determine a non-therapeutic treatment to be recommended, the captured features of the examined surface area 12 may be compared with application areas, effects and application instructions of treatment products and/or care instructions. Information about the treatment products and/or treatment instructions may be stored in a data storage unit 140.

The data storage unit 140 may exist outside and spatially separated from the evaluation unit 120. The evaluation unit 120 may access the data storage unit 140 via a data network 122 and interrogate information on the treatment products and/or treatment instructions stored there. This interrogated information is compared by the evaluation unit 120 with the recorded features of the surface area 12 to be examined in order to determine appropriate recommendations for the non-therapeutic treatment of the examined surface area. In other words, the data storage unit is interrogated using the determined body surface characteristics. From the data storage unit, a large amount of stored information can be interrogated and then filtered using the determined body surface characteristics and, if necessary, treatment goals to determine which of the treatment products and/or treatment instructions are relevant. For this purpose, the data may be loaded from the data storage unit into a random access memory. Alternatively, the determined body surface characteristics may be used when interrogating the information from the database to interrogate only the relevant information from the database. For the purposes of this description, these two variants may be regarded as equivalent in their effect.

The data network 122 may be a public data transmission network, which has sections with or without wires. For example, the evaluation unit 120 may establish a wireless connection to an access point (not shown) on the data network 122 in order to establish a corresponding connection to the data storage unit 140.

The user interface 130 is connected to the evaluation unit 120 via data transmission connection 124. The user interface 130 has an input unit 132 and an output unit 134. The input unit 132 allows a user to set parameters for the operation and configuration of the evaluation unit 120, the acquisition unit 110 and/or the user interface 130. The input unit 132 may record information via different interfaces: a keyboard, a mouse, a touch-sensitive display or via a microphone (so-called voice control). It is conceivable that any interface is used via which a human user can communicate with a computing unit and enter or transfer data. The output unit 134 may be a display or other display unit that provides visual information to a user. The output unit 134 may also include a loudspeaker, which may be used to output acoustic information. Visual information may be output on a touch-sensitive output unit, so that the output unit also allows a user to make entries.

The computer program enables the consumer to receive product recommendations for individually appropriate treatment products and/or application instructions based on the measurement of body surface characteristics on the output unit. The displayed products may be purchased through the input unit of the interface.

The evaluation unit 120 includes a processor 126 and a local memory 128. The processor 126 executes instructions to perform its intended function or functions. The local memory 128 can store the skin/hair features acquired by the acquisition unit 110 or the corresponding signals or values.

In this exemplary embodiment the evaluation unit 120 and the user interface 130 are located in a common enclosure 200. This common enclosure 200 also contains an energy storage 210, which supplies both the evaluation unit and the user interface with energy, preferably electrical energy. Thus the evaluation unit and the user interface may be operated independently, i.e. these units can perform the intended function without external power supply. In an example, the energy storage unit 210 may be intended to supply the acquisition unit 110 with electrical energy as well. This can be done via the data transmission connection 114.

It is a special aspect of this exemplary embodiment that the acquisition unit 110 may be operated with an evaluation unit 120 and a user interface 130, which are implemented in a portable device of a user or consumer. This makes it particularly easy to couple an acquisition unit 110, which enables advanced analysis and examination possibilities for a body surface (skin, hair) of a human user, with a portable computerized data processing device. The portable data processing device may be, for example, a smartphone or tablet and a home computer. The acquisition unit 110 may be connected or coupled mechanically, electrically and in terms of signaling to the portable data processing device by employing a defined interface.

Using this description in FIG. 1, further exemplary embodiments of set-up or arrangement 100 are described below.

In an exemplary embodiment a set-up or arrangement 100 for the determination of body surface characteristics is given. The set-up comprises an acquisition unit 110 for acquiring body surface features of a user; an evaluation unit 120 for evaluating the acquired body surface features and determining the body surface characteristics based on the acquired body surface features; and a user interface 130 comprising an output unit 134, the user interface being configured for interacting with a user. The evaluation unit 120 is adapted to perform or implement the following functions: to interrogate a data storage unit 140 using the determined body surface features; to obtain from the data storage unit 140 characteristics of treatment products and/or application instructions for non-therapeutic treatment of a body surface according to the determined body surface characteristics; and to instruct the output unit 134 to output information on the treatment products and/or application instructions to a user. In this exemplary embodiment the evaluation unit 120 is a portable computing unit and the acquisition unit is configured to acquire the body surface features by employing Multiple Spatially Resolved Reflection Spectroscopy (MSRRS) in a wavelength range between about 300 nm and about 1500 nm.

In other words, the set-up is configured to determine characteristics of a body surface or a portion of the body surface as described and, considering a desired or a predetermined target value or range of these characteristics, to select a treatment product and/or instructions for use for non-therapeutic treatment of the body surface and, if necessary, to output (visually, acoustically, or otherwise) or display instructions for use of the treatment product and further treatment instructions for the body surface. The treatment instructions may relate to a treatment product or be independent of it. For example, the treatment instructions may refer to what constitutes a desired and/or undesirable behavior in relation to the body surface characteristics recorded or determined and a given treatment objective. For example, treatment instructions may be to avoid contact of a body surface with water within a certain period of time after the application of a treatment product. The treatment instructions may also refer to nutritional advice and may be related to time of day, for example.

The acquisition unit 110 may also include its own energy storage (not shown). In such a case the acquisition unit 110 may also be connected wirelessly to the evaluation unit 120. The acquisition unit 110 is configured to detect characteristics and features of skin and/or hair by employing Multiple Spatially Resolved Reflection Spectroscopy. For this purpose, several light beams are emitted in the direction of skin/hair and partially reflected and absorbed. From the degree of reflection/absorption information about the condition and/or composition of the skin can be derived. By multiple use of Spatially Resolved Spectroscopy (SRS), light that has penetrated deep into the skin can be compared with light that has only passed through the outer layers of the skin/hair. This increases the measurement accuracy and is helpful for an exact measurement due to the complexity and inhomogeneity of the skin/hair. The accuracy can be further improved by different angles of incidence. The light measured by MSRRS may be used to determine the concentration of non-enzymatic antioxidants, e.g. carotenoids, in the skin.

In an exemplary embodiment, the acquisition unit has a large number of light emitters positioned side by side along one surface of the acquisition unit.

This can be called a light emitter array. The light emitters may be evenly or unevenly distributed over a surface. Thus, the acquisition unit may be used to detect a user's body surface, which corresponds approximately to the size of the surface of the acquisition unit. The principle of Spatially Resolved Spectroscopy is therefore applied several times by employing the plurality of light emitters, in that the plurality of light emitters is operated simultaneously to emit light in the direction of the body surface.

In a further exemplary embodiment, the plurality of light emitters is configured to emit light at different wavelengths.

For example, a first group of light emitters may emit light of a first wavelength from the above-mentioned wavelength ranges and a second group of light emitters may emit light of a second wavelength different from the first wavelength from the above-mentioned wavelength ranges. It is of course possible that the total number of light emitters is divided into more than two groups, each light emitter typically being assigned to only one of these groups. A light emitter can emit light of a certain wavelength depending on its design. However, it is also conceivable to use light emitters whose wavelength can be changed or adapted. It is also conceivable that each light emitter emits light of a specifically assigned wavelength. This means that the wavelength of each light emitter is different from the wavelength of any other light emitter. This means that as many different wavelengths can be emitted as there are light emitters.

In a further exemplary embodiment, the multitude of light emitters is configured to emit light at different angles of incidence.

This means that at least two light emitters are not aligned parallel and that the angles at which the emitted light from these two light emitters impinges on the body surface differ from each other. Several light emitters may be combined into groups, where the light emitters of one group have the same angle of incidence and this angle of incidence is different from the angle of incidence of another group. It is conceivable that each light emitter has an individual angle of incidence which differs from the angle of incidence of all other light emitters. The angle of incidence may also be described as the angle between the direction of the emitted light of a light emitter and the surface 111 (see FIG. 4) of the acquisition unit.

In a further exemplary embodiment, the acquisition unit includes a large number of light detectors positioned side by side along one surface of the acquisition unit.

The light detectors are configured to detect the light reflected from the body surface and to convey the reflected light (e.g. intensity, wavelength) for further evaluation in order to allow conclusions to be drawn about the characteristics of the body surface. It may be necessary to use the wavelengths and the angles of incidence of the emitted light to evaluate the detected signals.

In a further exemplary embodiment, the plurality of light detectors is configured to detect light at different wavelengths.

Thus the light detectors are adapted to the use of different wavelengths by the light emitters.

The light detectors may be preceded by an optical filter element. This means that the light beams must pass through the optical filter element before they reach the light detectors. The filter element may be a variable filter element, i.e. the wavelength of the light passed varies depending on an adjustment parameter. The filter element may also be configured to allow different wavelengths to pass for different light detectors.

In an exemplary embodiment the evaluation unit 120 and the user interface 130 are housed in a common enclosure 200.

In an exemplary embodiment, the set-up also includes an energy storage 210, which is located in the enclosure 200 to supply the evaluation unit 120 and the user interface 130 with energy, in order to enable at least temporarily an autonomous operation of the evaluation unit and the user interface without connection to an external energy source.

This means that the evaluation unit 120, the user interface 130 and also the acquisition unit 110 may be operated self-sufficiently and without external power supply as intended. The energy storage 210 is preferably a rechargeable energy storage.

In an exemplary embodiment the evaluation unit 120 is configured to reach the data storage unit 140 via a data network 122.

This means that the data storage unit 140 is spatially separated from the evaluation unit 120. For example, the data storage unit 140 is configured in such a way that a plurality of set-ups or arrangements 100 may access the data storage unit 140 as described herein. This makes it possible that the data storage unit 140 may be filled with information on treatment products and/or treatment instructions at a central location. Thus, current information may be delivered to interrogating set-ups or arrangements 100.

In an exemplary embodiment, the evaluation unit 120 is configured to compare the features of treatment products for the non-therapeutic treatment of a body surface with the determined body surface characteristics and to determine an effect of the treatment products on the body surface, taking into account the determined body surface characteristics and, if necessary, a specifiable treatment objective (e.g. a desired or achievable condition of the body surface characteristics).

This means that the treatment products are selected according to the body surface characteristics determined and displayed on the user interface.

In an exemplary embodiment, the evaluation unit 120 is configured to obtain information on the non-therapeutic treatment of a body surface from the data storage unit 140 according to the determined body surface characteristics and to instruct the output unit 134 to display the information obtained.

These instructions may be general instructions (without reference to a specific treatment product) concerning the treatment of skin and hair, but may also be instructions relating to a specific treatment product. The instructions may also include explanations, which behaviors influence which characteristics of the body surface (especially skin and/or hair) and how.

The data storage unit 140 may contain information from dermatological studies and information from literature sources and/or scientific publications. The evaluation unit 120 may be configured to display or at least point out to a user an extract of this information depending on the body surface characteristics recorded.

In a further example, the evaluation unit 120 is configured to request information from a user and to take this information into account when interrogating the data storage unit 140 in order to obtain from the data storage unit 140 features of treatment products for the non-therapeutic treatment of a body surface according to the requested information.

The requested information may be recorded by employing a predefined questionnaire, in which a statement by the user is given more or less weight or is selected from one of several possible answers. The given questionnaire may deal in particular with the user's habits and extraordinary stresses and strains, e.g. dietary habits, duration and quality of sleep, amount to be drunk, type of drinks, use of stimulants (e.g. nicotine, alcohol), professional and leisure activities (a lot of time outside of buildings in all weather conditions, stay in the mountains, visit to a solarium). The information requested may also relate to a desired or achievable property of the body surface.

In an exemplary embodiment the evaluation unit 120 includes a local memory 128, which is configured to persistently store the data interrogated by the data storage unit.

This means that the evaluation unit 120 may at least temporarily perform its functions without having to rely on a permanent connection to the data storage unit 140, because the interrogated data is stored in the local memory. The data is stored in the local memory 128 in such a way that it is retained when the evaluation unit 120 is switched off or shut down (persistent storage). It is possible that the evaluation unit 120 will only interrogate data from the data storage unit 140 that matches a current image or current characteristics of skin and hair. In an exemplary embodiment it is also possible to request and locally store such data that is not compatible with slightly changed characteristics of skin and hair based on the current state. It is therefore not necessary to interrogate all data from the data storage unit 140 and store it in the local memory 128. Rather, it is possible to transfer specific data or information from the data storage unit 140 to the local memory 128 that matches the recorded condition of skin and hair.

In a further exemplary embodiment, the evaluation unit 120 is configured to store the determined body surface characteristics in the local memory 128 with a time stamp relating to the determination of the body surface characteristics.

This makes it possible to observe and analyze changes in the body surface over time. Thus, these changes may also be used to provide suitable non-therapeutic treatment products and/or treatment instructions. Furthermore, this exemplary embodiment enables a user to observe the changes in order to determine the achievement of or approach to self-defined goals.

In an exemplary embodiment the evaluation unit 120 is configured to store the determined body surface characteristics over a longer period of time comprising at least two processes of recording the body surface characteristics in the local memory 128 and optionally to call up a development of the body surface characteristics over a specifiable period of time from the local memory and to instruct the output unit 134 to display this development.

In an exemplary embodiment the evaluation unit 120 is configured to transfer the determined body surface characteristics to the data storage unit 140.

The determined and transferred body surface characteristics may be assigned to an identification number or an identifier of a user in the data storage unit 140, so that a user may view his data from different devices. This method also has the advantage that a user's data is stored at a central location in case of loss or defect of the personal evaluation unit 120.

Furthermore, this exemplary embodiment allows to record body surface characteristics of a user over a longer period of time and to observe their changes and, if necessary, to link them to recommendations for non-therapeutic treatment products and/or treatment instructions.

As already mentioned above, the body surface characteristics are characteristics of the skin and/or hair of a human user of the set-up or arrangement 100. In particular the set-up or arrangement 100 or the acquisition unit 110 is configured to examine those parts of the skin and hair of a human user which are exposed to the environment, in particular hands/arms, legs/feet, face and main hair. Of course, this does not exclude the possibility that the acquisition unit 110 can also examine other parts of a human body and record their characteristics, i.e. those parts which are not usually exposed to environmental influences over a longer period of time, such as the upper body (back, chest, abdomen) and intimate area/buttocks.

In an exemplary embodiment the set-up or arrangement 100 is configured to give instructions for the operation of the acquisition unit visually on the output unit 134 and/or acoustically via a loudspeaker. This may be particularly helpful when the surface of a user's body is being comprehensively scanned for the first time in order to obtain an overview of the condition of the skin or hair.

In an exemplary embodiment, the output unit is configured to output information concerning ingredients and/or composition of a treatment product and/or application instructions for the non-therapeutic treatment of a body surface.

This enables a user to form his own opinion about a treatment product in its entirety. In addition, application instructions may be given to the user in relation to a treatment product or independently of it. The application instructions may relate to desired and/or unwanted behavior.

The acquisition unit 110 is configured to detect body surface features by employing Multiple Spatially Resolved Reflection Spectroscopy in a wavelength range between about 300 nm and about 1500 nm.

The acquisition unit 110 is preferably configured to use wavelengths of about 350 nm or about 1000 nm. These wavelengths may be particularly advantageous for detecting characteristics of human skin and/or human hair.

In an exemplary embodiment, the user interface is configured to receive an input from a user after the output of features of a treatment product and to initiate an action concerning the displayed treatment product based on this input.

The action may, for example, relate to the fact that a treatment product is offered for sale to the user and that the user may initiate the purchase by employing an input. In addition to the purchase of treatment products, the user may also be offered further information on the purchase. This additional information may refer to more detailed treatment and application instructions. For example, the program receives the request that the user wishes to purchase the treatment, stores the request and/or transmits the request to a trading company that distributes the treatment products. The user is asked by the computer program to enter his personal data (address, bank information, shipping preference, etc.) via the input unit. Alternatively, the user may be shown where he can purchase the treatment product.

In summary, the set-up or arrangement 100 for determining body surface characteristics of a human user includes a combination of an acquisition unit 110, which is configured to determine body surface features by employing Multiple Spatially Resolved Reflection Spectroscopy in a wavelength range between about 300 nm and about 1500 nm, and a portable device, which includes an evaluation unit 120 and a user interface 130 in a common enclosure. The portable device may, for example, be a personal, portable, computerized device which is configured to receive measured values from the acquisition unit 110 and, based on these measured values and using an external data storage unit 140, to determine and display to the user recommendations for non-therapeutic treatment products and treatment instructions. This design allows the user to use the acquisition unit 110 together with the portable device in a personal/private environment. The portable device may perform a variety of different functions for the user, whereby use in combination with the acquisition unit 110 is only one of several functions.

FIG. 2 shows a data storage device 300 with a computer program product 310, which is configured to run on a portable computing unit 120 and instructs a processor 126 of the portable computing unit to perform the following steps: detecting body surface features of a user by employing Multiple Spatially Resolved Reflection Spectroscopy in a wavelength range between about 300 nm and about 1500 nm; evaluating the determined body surface features and determining body surface features based on the detected body surface characteristics; interrogating a data storage unit 140 using the determined body surface features; obtaining features of treatment products and/or application instructions for non-therapeutic treatment of a body surface according to the determined body surface characteristics from the data storage unit 140; and instructing the output unit (134) to output information on the treatment products and/or application instructions.

The data storage device 300 may use magnetic, optical or electrical storage technologies (or combinations thereof) to hold the instructions of the computer program product in a machine-readable form. These instructions may be used to be executed directly by the processor 126 of the portable computing unit 120 (the evaluation unit 120 from the exemplary embodiment in FIG. 1). Alternatively, the instructions may be used to load the computer program product 310 into an internal memory of the portable computing unit 120 for execution. This internal memory may be, for example, the local memory 128 shown in FIG. 1.

The computer program product 310 may be downloaded via a data network to a user's portable device and installed on the portable device for use by the user.

In addition to FIG. 2, FIG. 3 shows a method 400 with the following steps (these steps correspond to the functions of the computer program product 310 shown in FIG. 2): in a first step 410, body surface features of a user are detected by employing Multiple Spatially Resolved Reflection Spectroscopy in a wavelength range between about 300 nm and about 1500 nm; in a second step 420, the detected body surface features are evaluated and body surface characteristics are determined based on the detected body surface features; in a third step 430, a data storage unit 140 is interrogated using the determined body surface characteristics (this may mean, for example, that the body surface characteristics are transferred to the data storage unit 140 and the data storage unit returns data or information in response thereto); in a fourth step 440, features of treatment products and/or application instructions for non-therapeutic treatment of a body surface according to the determined body surface characteristics are transmitted from the data storage unit 140 and received by the portable computing unit 120; and finally, in a fifth step 450, the output unit 134 is instructed to output information on the treatment products or with respect to the treatment instructions.

The computer program product 310 contains instructions which instruct the processor 126 of the portable computing unit 120 to perform these steps 410 to 450.

Needless to say, method 400 or its steps 410 to 450 may be modified in accordance with one of the exemplary embodiments of set-up or arrangement 100, as shown with reference to FIG. 1 and the rest of the description. This means that the functions of set-up or arrangement 100 or one of its components described herein, in particular of the evaluation unit 120, may be implemented as a step of method 400. No repetition of the functions of the evaluation unit is given here. Rather, the expert will recognize that and how these functions are implemented as method steps.

The different method steps as well as the components of the set-up may be implemented by one or more circuits. In an embodiment, a "circuit" is to be understood as any unit that implements a logic, which may be hardware, software, firmware or a combination of these. Thus, in an embodiment, a "circuit" may be a hard-wired logic circuit or a programmable logic circuit, such as a programmable processor, e.g. a microprocessor or a field-programmable gate array (FPGA) module. A "circuit" may also include a processor that executes software, such as any type of computer program, such as a computer program in programming code for a virtual machine (delimited run-time environment, virtual machine), such as a Java computer program. A "circuit" may be understood in an embodiment to mean any type of implementation of the functions described below.

Figure 4:
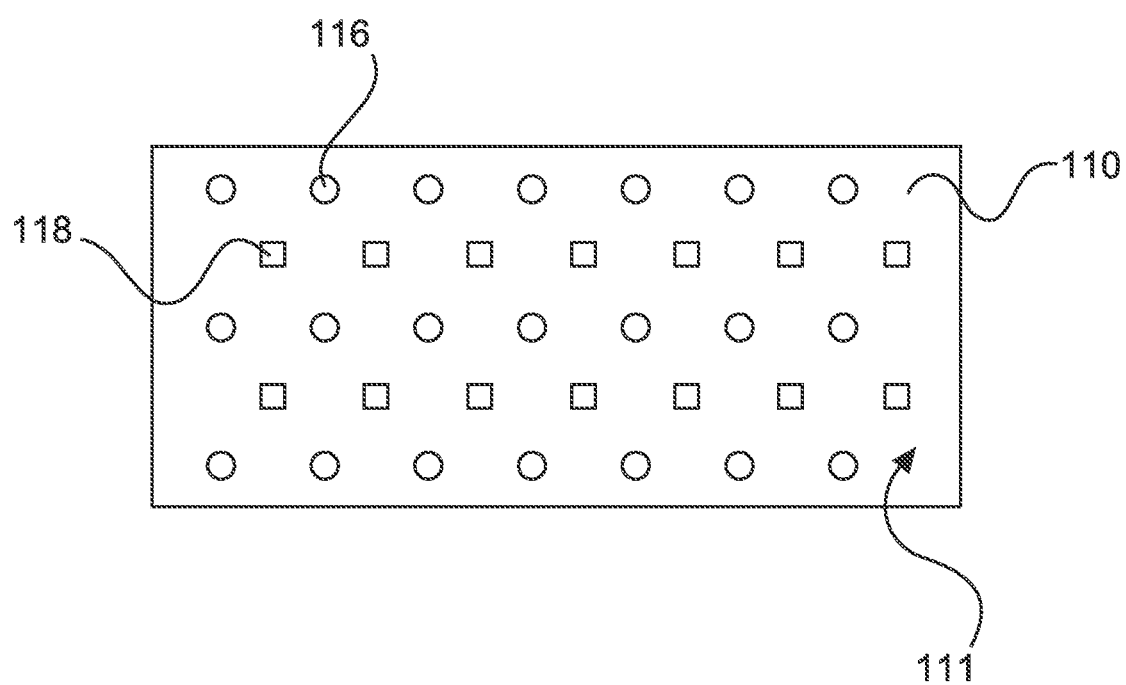
FIG. 4 a schematic illustration of an acquisition unit for a set-up or arrangement according to a further exemplary embodiment.

FIG. 4 shows a schematic diagram of an acquisition unit 110, which has a surface 111 with a large number of light emitters 116 and a large number of light detectors 118. The light emitters 116 are shown as circles and the light detectors 118 are shown as squares. Although in FIG. 4 the light emitters 116 and the light detectors 118 are placed in unmixed rows (i.e. one row has either only light detectors or only light emitters), different set-ups of these elements are also possible. For example, light emitters and light detectors may be placed alternately in a row. The rows may be offset laterally to each other to increase the density of light detectors or light emitters on surface 111.

From the acquisition unit 110, the surface that is facing the skin of a user during a detection process is visible. In other words, the light emitters 116 emit the light rays from the drawing plane towards an observer.

The processor 126 (FIG. 1) may implement control functions and issue control commands to the light emitter(s) 116. For example, the processor 126 may control the light emitter to emit a light beam of a certain intensity, wavelength or duration (these may be called parameters of a light beam). The light beams may be output in pulses. After a certain interval, a further light pulse is output. The further light pulse may be similar to the previous light pulse (i.e. the values of its parameters are the same), but may also be different. It is conceivable, for example, that two successive light pulses differ in one parameter or even in more than one parameter. For example, if the pulse duration and wavelength are constant, the intensity may be changed. Such a change may follow a given pattern and affect a large number of consecutive pulses. By varying the parameters, the response of the body surface may be measured over a broad spectrum or range of values of the parameters in question. The light pulse or pulses may be laser pulses.

The evaluation unit 120 with the processor 126 (FIG. 1) also receives the signals from the light detector 118 and may classify the examined body surface based on these signals. In other words, the signals delivered by the light detector 118 are characteristic of the body surface. These signals may also be referred to as signal patterns and may be used to determine and output a product recommendation and/or application instructions.

It is conceivable that a typical signal pattern is assigned to a product and/or application instruction, where the product and/or application instruction may be used sensibly. This assigned signal pattern of the products and/or the application instructions may be compared with the actual signal pattern. From a certain degree of correspondence of the signal pattern detected or supplied by the light detector with the signal pattern assigned to the products and/or application instructions, the corresponding products and/or application instructions may then be issued. The signals may be examined for qualitative similarity (do the shapes or courses of the signals correspond) and/or quantitative similarity (do the signals have similar input values, i.e. light pulses, similar output values, i.e. ultrasonic signals).

It is also conceivable that, depending on user input, a factor may be determined which is applied to the signal detected by the detector before this input signal is compared with the signal patterns of the products or application instructions. This has the advantage that a correction factor may be applied to the detected signal to improve the accuracy of the product recommendations and/or application instructions for a particular user.

In an exemplary embodiment the light detector is configured to generate a signal pattern based on the received signals, which is characteristic for the body surface characteristics.

This means that no absolute values for body surface characteristics need to be determined. Rather, it may be sufficient to use the received signal patterns of the light detector to determine a product recommendation and/or application instruction. For example, body surfaces may be examined to determine a typical signal pattern of the light detector. Independently of this, it is then possible to determine which products and/or application instructions make sense for the body surface under investigation. The products and/or application instructions thus determined may then be assigned the corresponding signal pattern to express that these products and/or application instructions are suitable for a body surface with this signal pattern. This means that finding a suitable product recommendation is simplified because only the determined signal patterns of the body surface have to be compared with signal patterns assigned to the products and/or application instructions.

The surface 111 may be rectangular or square. In a typical configuration the surface is about 20 mm×about 20 mm and contains over 100 light emitters and over 100 light detectors. The number of light detectors may be greater than the number of light emitters in order to detect the light emitted by a light emitter at different locations.

LIST OF REFERENCE SIGNS

10 Analysis object
12 Surface area to be examined
100 Set-up or arrangement for the determination of skin characteristics
110 Acquisition unit
111 Surface
112 Electromagnetic waves
114 Data transmission connection
116 Light emitter
118 Light detector
120 Evaluation unit
122 Data network
124 Data transmission connection
126 Processor
128 Local memory
130 User interface
132 Input unit
134 Output unit
140 Data storage unit
200 Enclosure
210 Energy storage
300 Data storage device
310 Method
410-450 Method steps While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An arrangement for determining body surface characteristics, the arrangement comprising:
   an acquisition unit configured to detect body surface features by Multiple Spatially Resolved Reflection Spectroscopy (MSRRS) in a wavelength range between about 300 nm and about 1500 nm;
   a data storage unit to interrogate data using the determined body surface characteristics;
   a user interface comprising an output unit, wherein the user interface is configured to interact with a user; and
   a portable computing unit configured for:
      interacting with a user and for evaluating the determined body surface features and for determining the body surface characteristics based on the determined body surface features;
      obtaining from the data storage unit features of treatment products and/or application instructions for non-therapeutic treatment of a body surface according to the determined body surface characteristics; and
      instructing the output unit to output information on the treatment products and/or application instructions to a user,
      wherein the portable computing unit is further configured to compare the features of treatment products for non-therapeutic treatment of a body surface with the determined body surface characteristics and to determine an effect of the treatment products on the body surface, taking into account the determined body surface characteristics.

2. The arrangement according to claim 1, wherein the acquisition unit comprises a plurality of light emitters positioned side by side along a surface of the acquisition unit.

3. The arrangement according to claim 2, wherein the plurality of light emitters are configured to emit light at different wavelengths.

4. The arrangement according to claim 2, wherein the plurality of light emitters are adapted to emit light at different angles of incidence.

5. The arrangement according to claim 1, wherein the acquisition unit comprises a plurality of light detectors positioned side by side along a surface of the acquisition unit.

6. The arrangement according to claim 5, wherein the plurality of light detectors are configured to detect light at different wavelengths.

7. The arrangement according to claim 1, further comprising an enclosure and an energy storage, wherein the portable computing unit and the user interface are accommodated in the enclosure, and wherein the energy storage is positioned in the enclosure in order to supply the evaluation unit and the user interface with energy, and in order to enable at least temporarily an autonomous operation of the evaluation unit and the user interface without connection to an external energy source.

8. The arrangement according to claim 1, wherein the output unit is configured to output information regarding one or more of ingredients, composition of a treatment product, and application instructions for non-therapeutic treatment of a body surface.

9. The arrangement according to claim 1, wherein the user interface is configured to receive an input from a user after issuing features of a treatment product and/or application instructions and to initiate an action regarding the displayed treatment product and/or application instructions based on this input.

10. The arrangement according to claim 9, wherein the user interface is configured to offer the treatment product for purchase by the user and to initiate the purchase upon the user's input.

11. The arrangement according to claim 1, wherein the acquisition unit is configured to use wavelengths between about 440 nm and about 490 nm.

12. An arrangement for determining body surface characteristics, the arrangement comprising:
   an acquisition unit configured to detect body surface features by Multiple Spatially Resolved Reflection Spectroscopy (MSRRS) in a wavelength range between about 300 nm and about 1500 nm;
   a data storage unit to interrogate data using the determined body surface characteristics;
   a user interface comprising an output unit, wherein the user interface is configured to interact with a user; and
   a portable computing unit configured for:
      interacting with a user and for evaluating the determined body surface features and for determining the body surface characteristics based on the determined body surface features;
      obtaining from the data storage unit features of treatment products and/or application instructions for non-therapeutic treatment of a body surface according to the determined body surface characteristics; and
      instructing the output unit to output information on the treatment products and/or application instructions to a user,
      wherein the portable computing unit is further configured to obtain from the data storage unit information on the non-therapeutic treatment of a body surface according to the determined body surface characteristics and to instruct the output unit to display the obtained information.

13. An arrangement for determining body surface characteristics, the arrangement comprising:
   an acquisition unit configured to detect body surface features by Multiple Spatially Resolved Reflection Spectroscopy (MSRRS) in a wavelength range between about 300 nm and about 1500 nm;
   a data storage unit to interrogate data using the determined body surface characteristics;
   a user interface comprising an output unit, wherein the user interface is configured to interact with a user; and
   a portable computing unit configured for:
      interacting with a user and for evaluating the determined body surface features and for determining the body surface characteristics based on the determined body surface features;

obtaining from the data storage unit features of treatment products and/or application instructions for non-therapeutic treatment of a body surface according to the determined body surface characteristics; and instructing the output unit to output information on the treatment products and/or application instructions to a user, wherein the portable computing unit is further configured to request information from a user and to additionally take this information into account when requesting the data storage unit in order to obtain from the data storage unit features of treatment products for non-therapeutic treatment of a body surface according to the interrogated information.

* * * * *